United States Patent
Parisi et al.

(10) Patent No.: US 6,648,874 B2
(45) Date of Patent: *Nov. 18, 2003

(54) GUIDE CATHETER WITH LUBRICIOUS INNER LINER

(75) Inventors: Mary Parisi, Chaska, MN (US); Martin Willard, Maple Grove, MN (US); Yiqun Wang, Maple Grove, MN (US); Robert John Bianchi, Minneapolis, MN (US); Timothy L. Rubesch, Brooklyn Center, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,721

(22) Filed: Feb. 28, 2000

(65) Prior Publication Data

US 2001/0027310 A1 Oct. 4, 2001

(51) Int. Cl.[7] .............................................. A61M 25/00
(52) U.S. Cl. ..................................................... 604/525
(58) Field of Search ................................. 604/523–527, 604/264, 529; 600/433–435, 585; 138/130–132, 125, 129, 144; 606/1, 13–14, 20–22, 27, 32, 41; 607/113–125

(56) References Cited

U.S. PATENT DOCUMENTS

| | | | |
|---|---|---|---|
| 4,385,635 A | 5/1983 | Ruiz ........................... 128/658 |
| 4,563,181 A | 1/1986 | Wijayarathna et al. ...... 604/280 |
| 4,596,563 A | 6/1986 | Pande .......................... 604/264 |
| 4,636,346 A * | 1/1987 | Gold et al. .................. 264/139 |
| 4,665,604 A | 5/1987 | Dubowik ...................... 29/415 |
| 4,863,442 A | 9/1989 | DeMello et al. ............. 604/282 |
| 4,886,506 A | 12/1989 | Lovgren et al. ............. 604/280 |
| 5,061,257 A | 10/1991 | Martinez et al. ............. 604/282 |
| 5,078,702 A | 1/1992 | Pomeranz .................... 604/280 |
| 5,221,270 A | 6/1993 | Parker ......................... 604/282 |
| 5,234,416 A | 8/1993 | Macaulay et al. ........... 604/282 |
| 5,254,107 A | 10/1993 | Soltesz ........................ 604/282 |
| 5,509,910 A | 4/1996 | Lunn ........................... 604/282 |
| 5,531,721 A | 7/1996 | Pepin et al. ................. 604/282 |
| 5,545,149 A | 8/1996 | Brin et al. ................... 604/265 |
| 5,545,151 A | 8/1996 | O'Connor et al. .......... 604/282 |
| 5,569,218 A | 10/1996 | Berg ........................... 604/282 |
| 5,599,319 A | 2/1997 | Stevens ....................... 604/264 |

FOREIGN PATENT DOCUMENTS

WO    WO 99/17829    4/1999

OTHER PUBLICATIONS

"Hyflon®," Information Sheet, date unknown, 5 pages.

*Primary Examiner*—LoAn H. Thanh
(74) *Attorney, Agent, or Firm*—Crompton, Seager & Tufte, LLC

(57) ABSTRACT

A catheter shaft is disclosed utilizing perfluoroalkoxy polytetrafluoroethylene (PFA) as a lubricious inner lumen for which to aid the advancement of additional medical devices. PFA possesses adequate lubricity while requiring no special fabricating techniques. Thus, PFA may be processed by conventional melt-extrusion techniques, as well as by injection, compression, rotational transfer, and blow molding processes; optimizing the manufacturability of the lubricious inner lumen. Additionally, the catheter shaft includes portions of the outer tubular member modified through an ablation process. The ablation process selectively removes extruded polymeric material around and between the contours of a braided support layer. In one illustrative embodiment, a portion of the outer layer of the catheter is removed by laser ablation and then refilled by polymeric inserts having various flexibility characteristics.

13 Claims, 4 Drawing Sheets

U.S. PATENT DOCUMENTS

| | | | |
|---|---|---|---|
| 5,599,325 A | 2/1997 | Ju et al. | 604/282 |
| 5,603,705 A | 2/1997 | Berg | 604/282 |
| 5,674,208 A | 10/1997 | Berg et al. | 604/282 |
| 5,676,659 A | 10/1997 | McGurk | 604/282 |
| 5,762,637 A | 6/1998 | Berg et al. | 604/264 |
| 5,769,830 A | 6/1998 | Parker | 604/282 |
| 5,792,124 A | 8/1998 | Horrigan et al. | 604/282 |
| 5,795,341 A | 8/1998 | Samson | 604/282 |
| 5,820,612 A | 10/1998 | Berg | 604/282 |
| 5,836,925 A | 11/1998 | Soltesz | 604/280 |
| 5,891,114 A | 4/1999 | Chien et al. | 604/282 |
| 5,897,537 A | 4/1999 | Berg et al. | 604/282 |
| 5,911,715 A | 6/1999 | Berg et al. | 604/525 |
| 5,938,587 A | 8/1999 | Taylor et al. | 600/139 |
| 5,938,653 A | 8/1999 | Pepin | 604/527 |
| 5,954,651 A | 9/1999 | Berg et al. | 600/434 |
| 5,971,975 A * | 10/1999 | Mills et al. | 604/527 |

\* cited by examiner

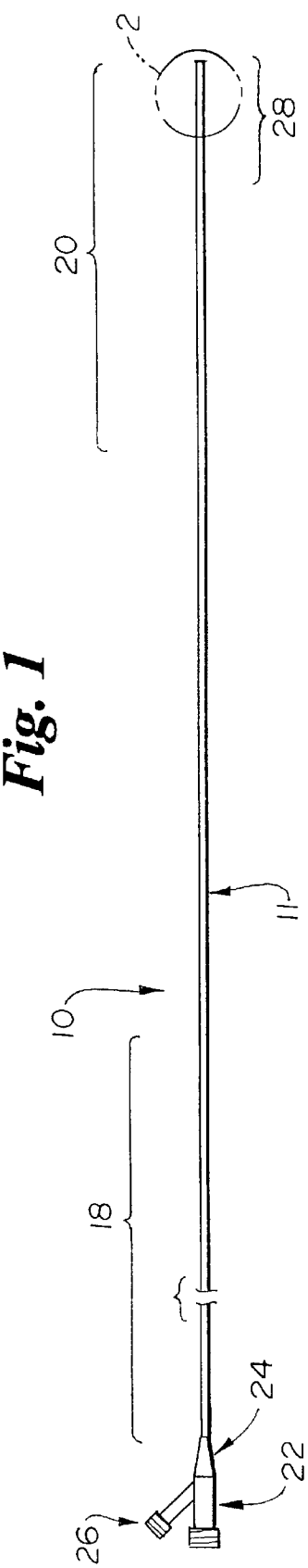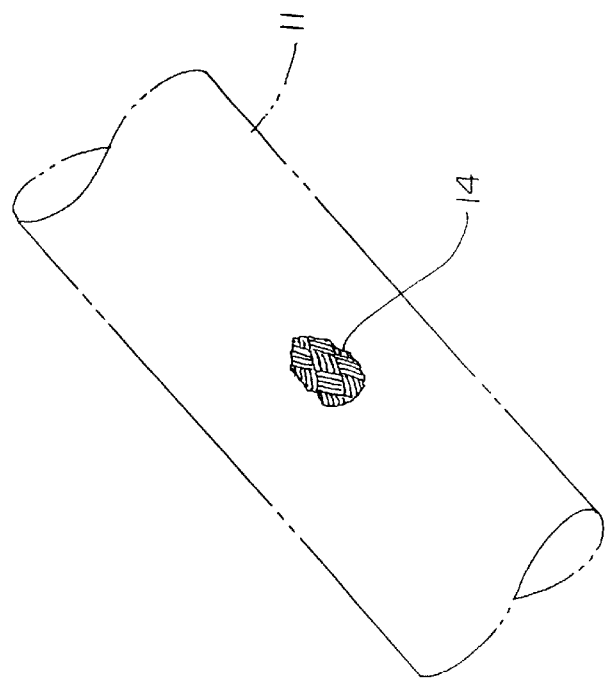

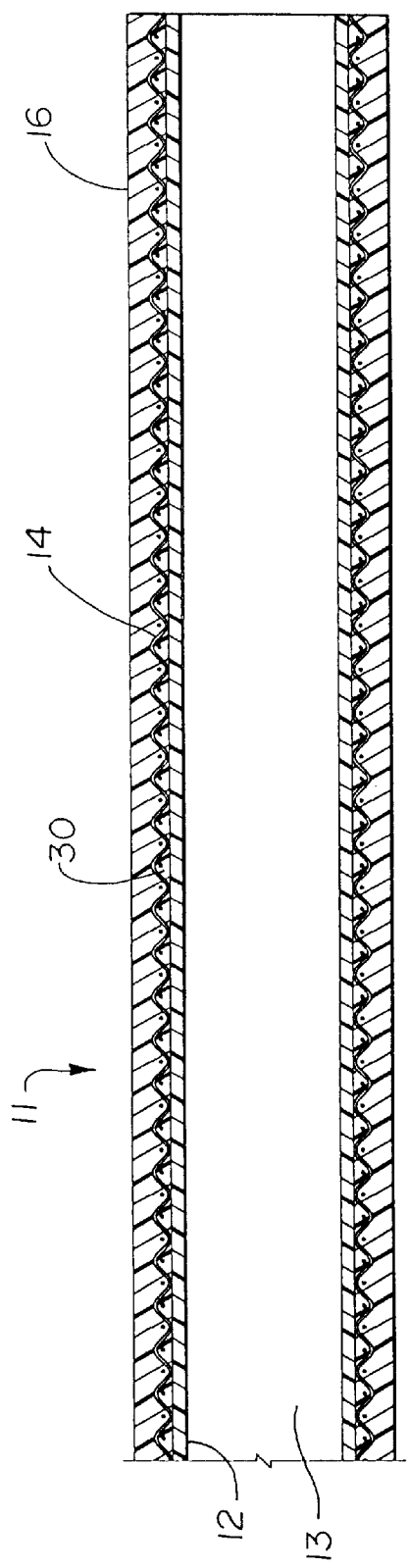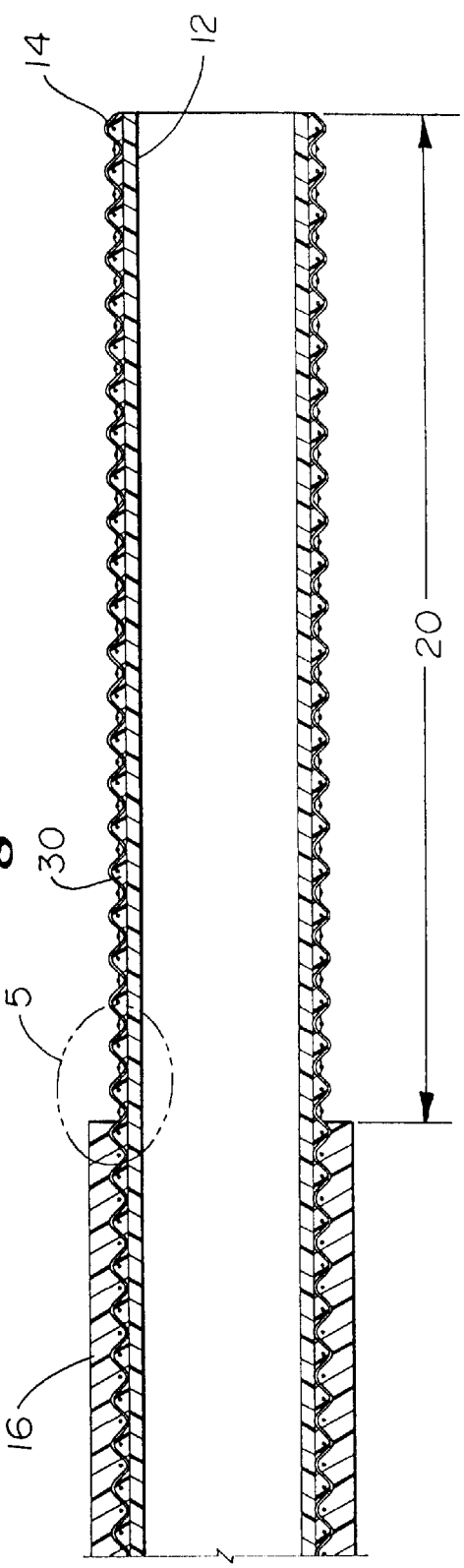

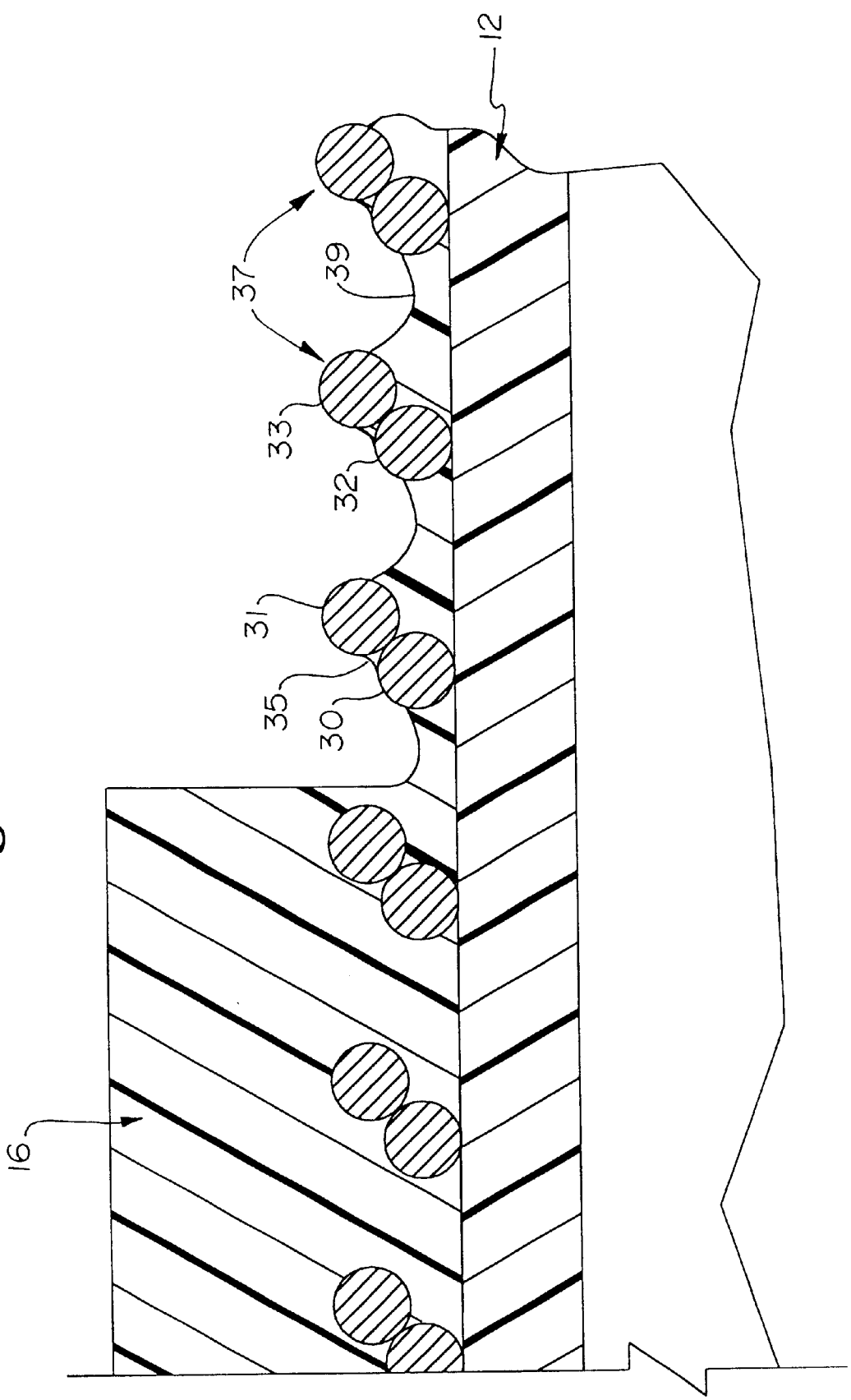

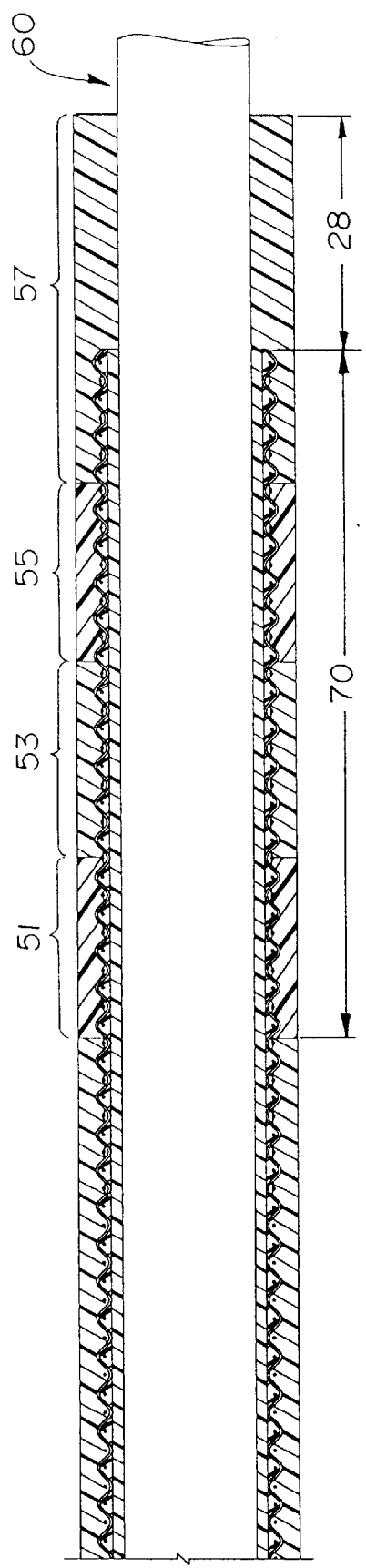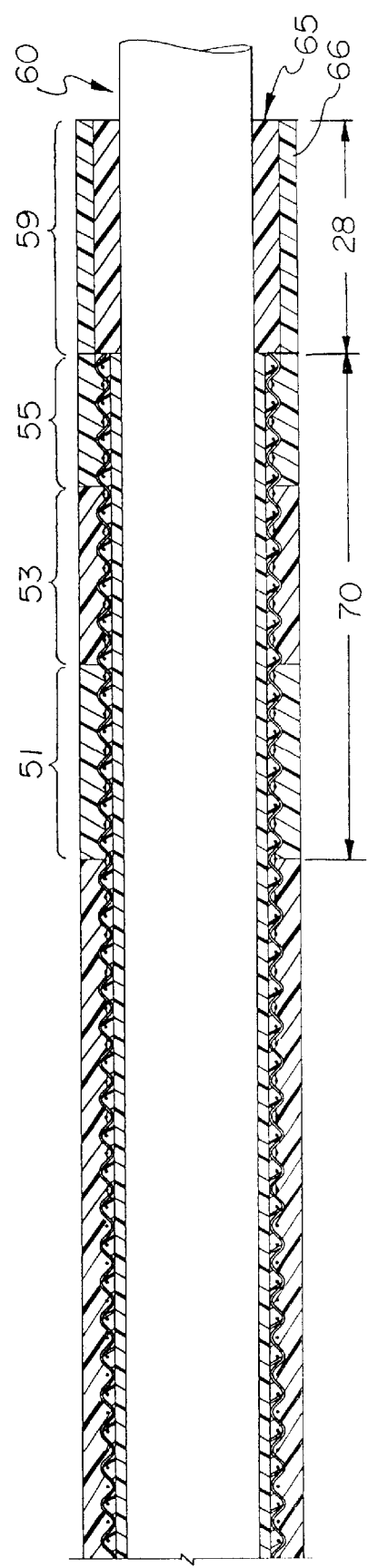

GUIDE CATHETER WITH LUBRICIOUS INNER LINER

TECHNICAL FIELD

The present invention generally relates to the field of intravascular medical devices, and more specifically to the field of guide catheters for placing balloon catheters and other similar diagnostic or therapeutic catheters within the body for treatment and diagnosis of diseases. In particular, the present invention relates to an improved guide catheter shaft design and corresponding methods of manufacture.

BACKGROUND OF THE INVENTION

Several types of catheters are utilized for intravascular treatment. Examples of intravascular catheters include guide catheters, angioplasty catheters, stent delivery devices, angiographic catheters, neuro catheters, and the like.

Guide catheters are commonly used during coronary angioplasty procedures to aid in delivering a balloon catheter or other interventional medical devices to a treatment site in a vessel or other lumen within the body. In a routine coronary angioplasty procedure, a guiding catheter is introduced into a peripheral artery and advanced over a guidewire through the aorta until the distal end of the guide catheter is engaged with the appropriate coronary ostium. Next, a balloon dilatation catheter is introduced over the guidewire and through the guide catheter. The guidewire is advanced past the distal end of the guide catheter within the lumen of the diseased vessel and manipulated across the region of the stenosis. The balloon dilatation catheter is then advanced past the distal end of the guide catheter over the guidewire until the balloon is positioned across the treatment site. After the balloon is inflated to dilate the blood vessel in the region of the treatment site, the guidewire, balloon dilatation catheter and guide catheter can be withdrawn.

Guide catheters typically have preformed bends formed along their distal portion to facilitate placement of the distal end of the guide catheter into the ostium of a particular coronary artery of a patient. In order to function efficiently, guide catheters should have a relatively stiff main body portion and soft distal tip. The stiff main body portion gives the guide catheter sufficient "pushability" and "torqueability" to allow the guide catheter to be inserted percutaneously into a peripheral artery, moved and rotated in the vasculature to position the distal end of the catheter at the desired site adjacent to a particular coronary artery. However, the distal portion should have sufficient flexibility so that it can track over a guidewire and be maneuvered through a tortuous path to the treatment site. In addition, a soft distal tip at the very distal end of the catheter should be used to minimize the risk of causing trauma to a blood vessel while the guide catheter is being moved through the vasculature to the proper position.

Angiographic catheters can be used in evaluating the progress of coronary artery disease in patients. Angiography procedures are used to view the patency of selected blood vessels. In carrying out this procedure, a diagnostic catheter having a desired distal end curvature configuration may be advanced over a guidewire through the vascular system of the patient until the distal end of the catheter is steered into the particular coronary artery to be examined.

For most intravascular catheters, it is desirable to have both a small outer diameter and a large inner lumen. Having a small outer diameter allows the catheter to be maneuvered more easily once inserted into the body and may allow the catheter to reach more distal sites. Having a large inner lumen allows larger medical appliances to be inserted through the catheter and/or allow a higher volume of fluids to be injected through the inner lumen.

To aid the advancement of additional medical appliances through the catheter, the inner lumen is generally comprised of a lubricious polymer. Polytetrafluoroethylene (PTFE) is a lubricious polymer commonly utilized to form inner lumens for medical devices. Because of the material composition of PTFE, manufacturing processes are generally more limiting and time consuming.

To minimize the outer diameter of the catheter, and maximize the inner diameter of the inner lubricious lumen, a relatively thin catheter wall is needed. Thin-walled catheters generally lack sufficient strength to be useful in many medical procedures. Specifically, thin-walled catheters generally lack structural characteristics that aid a physician in routing the catheter through a patient's tortuous vasculature (i.e., pushability, torqueability, and kinkability, among others). One way to enhance the structural characteristics of such thin-walled catheters is to provide a reinforcing braid or coil in the catheter wall. The braided reinforcing layer can be braided over the lubricious layer, and the outer layer can be extruded over the reinforcing layer.

It is still often desired to modify portions of the catheter to further enhance the pushability, torqueability, and kinkability characteristics of the catheter. Because of the difficulty associated with extrusion of multiple polymers in different regions of a catheter's length, modifications are generally made ad hoc. These modifications generally involve removing material from specific portions of the catheter shaft and filling the voids with material having different physical properties than the material that was removed. Depending upon the desired effect, the regions may be filled with either more flexible material or more rigid material. Ultimately, changing the physical characteristics of a particular section of the catheter imparts new properties to the entire catheter.

SUMMARY OF THE INVENTION

The present invention provides a catheter shaft for use in a guide or diagnostic catheter with improved characteristics for accessing desired treatment sites. In a first preferred embodiment, the catheter shaft includes a distal shaft portion having an outer layer which has been at least partially removed through an ablation process to form a contoured outer surface generally following the contour of a braided support member therein. Tubular inserts are placed over the contoured surface to form an outer distal layer having desired flexibility characteristics for particular applications.

The catheter shaft generally includes an inner tubular member having a proximal portion, a distal portion, and a lumen extending longitudinally therethrough. The inner tubular member in preferably manufactured from a perfluoroalkoxy (PFA). The PFA has been found to provide sufficient lubricity for passing additional medical instruments through the lumen formed within the PFA inner tubular member. Further, the PFA is melt-processable, unlike polytetrafluoroethylene which has been used in prior guide or diagnostic catheters as a lubricious inner tubular member.

A support member is disposed over a substantial portion of the inner tubular member and conforms thereto. The support member layer is preferably an interwoven braided member made up of filaments which have been braided to conform to the outer surface of the inner tubular member. The exterior surface of the support member layer is generally contoured resulting from the weaving of the filaments. Further, it is preferred that at least one of the filaments of the support member layer is tungsten. The tungsten filament or filaments provides additional radiopacity to the shaft. It has been found that a combination of stainless steel filaments with tungsten filaments is preferred, with the tungsten filaments comprising no more than half of the total number of filaments. Desired flexibility characteristics are achieved with this combination. In a preferred embodiment, the tungsten filaments comprise no more than four of the total number of filaments.

A first outer tubular member is disposed over a substantial portion of the support member layer and the inner tubular member and conforming thereto. The first outer tubular member has a proximal portion and a distal portion. The distal portion of the outer tubular member has an outside diameter less than the outside diameter of the proximal portion. The distal portion of the outer tubular member has an outside surface which generally follows or conforms to the contour of the support member layer. A second outer tubular member is disposed over at least a portion of the distal portion of the first outer tubular member with the inside surface of this layer following the contour of the underlying layer and support member. In preferred embodiments, the second outer tubular member includes several tubular inserts which abut one another longitudinally. Each of the tubular inserts is selected for its particular performance characteristics, such as flexibility, to selectively form portions of the catheter shaft with desired flexibility. In this way, the flexibility of the overall catheter may be made to increase distally and terminate in a flexible distal tip. The user of discrete outer tubular member inserts or segments is disclosed in commonly assigned co-pending U.S. application Ser. No. 09/313,672, filed on May 18, 1999, entitled GUIDE CATHETER HAVING SELECTED FLEXURAL MODULUS SEGMENTS, the disclosure of which is incorporated herein by reference.

BRIEF DESCRIPTION OF THE DRAWINGS

FIG. 1 is a cross-sectional side view of a guide catheter in accordance with the present invention;

FIG. 2 is a partial cross-sectional side view of the guide catheter illustrating the basic members forming the catheter shaft;

FIG. 3 is a partial perspective view of the guide catheter illustrating the orientation of the support member layer disposed over the inner tubular member;

FIG. 4 is a partial cross-sectional side view of the distal portion of the outer tubular member after ablation;

FIG. 5 is a partial perspective view detailing the distal portion of the outer tubular member following the contours of the support member layer;

FIG. 6 is a partial cross-sectional side view of the distal portion of the guide catheter with the addition of inserts disposed over the previously exposed contour regions of the distal portion of the outer tubular member; and FIG. 7 is a partial cross-sectional side view of the distal portion of the guide catheter showing a preferred distal tip.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes are provided for selected elements. Those skilled in the art will recognize that many of the examples provided have suitable alternatives that may be utilized.

FIG. 1 shows a sectional side view of a guide catheter 10 in accordance with the present invention. Catheter shaft 11 is comprised of an inner tubular member 12 that is surrounded by a support member layer 14. An outer tubular member 16 subsequently surrounds support member layer 14. These structural features of catheter shaft 11 are illustrated in greater detail in FIG. 2.

Guide catheter 10 has a proximal end 18 and a distal end 20. Located at the proximal end 18 of the guide catheter is a manifold 22. Manifold 22 is connected to catheter shaft 11 and further includes a strain relief 24. The manifold allows fluid communication with the catheter shaft 11 lumen 13. The manifold 22 generally contains ports 26 that allow for fluid-tight connections with the manifold 22 of guide catheter 10. A luer-lock fitting is an example of a fluid-tight fitting attached to the distal end of the manifold ports 26. The manifold 22, and the above-mentioned ports 26, generally allow for the engagement of additional medical devices. In illustration, a balloon catheter may be inserted through a port 26 on the manifold 22 and further into the inner tubular member 12 of the catheter shaft. Additionally, fluids may be transmitted through the manifold 22 and into the catheter shaft 11, allowing for their accurate dispersion at the distal end of the guide catheter 20, if so desired.

The distal end of the catheter comprises a distal tip 28. The design of the catheter distal tip 28 accommodates for accurate movement through the tortuous vasculature of the human body. Distal tip 28 is generally comprised of a soft material that minimizes trauma to the surrounding tissue as guide catheter 10 is advanced to, and ultimately engaged with, its final destination within the vasculature.

Distal tip 28 is generally attached to catheter shaft 11 through thermal processing. Because distal tip 28 is generally processed separately from the catheter shaft 11, distal tip 28 is highly modifiable to meet certain design specifications. Additional information concerning the materials, design, and manufacture of distal tip 28 is described in greater detail with respect to FIGS. 6 and 7.

As described above, the present invention is often used in combination with additional medical devices. In a preferred embodiment, the present invention is utilized as a guide catheter. Once the guide catheter has reached its final destination within the vasculature, a balloon dilation catheter may be inserted through the guide catheter's manifold 22 and advanced through, and out, the guide catheter's inner tubular member 12. Additionally, radiopaque fluid may also be advanced to the opening of the guide catheter via manifold ports 26 of the guide catheter.

In an alternate embodiment, the present invention may be utilized in conjunction with an endoscope. Similar to a guide catheter, the catheter may be inserted through the mouth within a lumen of an endoscope, or similar orifice, and advanced through the alimentary canal. Once the catheter is correctly positioned, other medical devices may be inserted through manifold 22 and advanced through the catheter's inner tubular member 12 to an ultimate destination within the body.

FIG. 2 is a partial cross-sectional side view of guide catheter 10 in FIG. 1 illustrating the structural features forming catheter shaft 11. In a preferred embodiment, inner tubular member 12 is a thin-walled PFA (perfluoroalkoxy polytetrafluoroethylene) tube. PFA is a copolymer of tetrafluoroethylene with perfluoroalkyl vinyl ether (more specifically, perfluoropropyl vinyl ether or perfluoromethyl vinyl ether). The resultant polymer contains a carbon-fluorine backbone chain, typical of PTFE, having perfluoroalkoxy side chains. Although similar in chemical structure to PTFE, PFA does not require special fabricating techniques. PFA provides a sufficiently lubricious surface (e.g., low coefficient of friction) while additionally offering the flexibility of thermoplastic processing. For example, PFA may be processed by conventional melt-extrusion techniques, as well as by injection, compression, rotational transfer, and blow molding processes. PFA optimizes the manufacturability of inner tubular member 12 for guide catheter 10. The result is an easily manufactured inner tubular member 12 having a smooth, lubricious surface for the passage of other devices through the guide catheter 10.

Although not limiting to the following dimension, in a preferred embodiment, inner tubular member 12 can have a thickness of generally 0.0015 inches or less throughout the member's length. Furthermore, the inner diameter of inner tubular member 12 is from about 0.045 to about 0.115 inches in diameter, depending on desired use. The appropriate diameter and thickness may be achieved by extrusion over an acetyl core, a silver-plated copper core, or by free extrusion. An advantage of using a PFA inner tubular member is that an acetyl core may be used in lieu of a copper core, with the copper core required for PTFE manufacturing due to higher processing temperatures.

FIG. 2 further illustrates support member layer 14 applied over inner tubular member 12. In a preferred embodiment, support member layer 14 comprises two or more interwoven braided filaments 30 that extend over the length of catheter shaft 11. A preferred braid possesses a constant 2/2 weave having a pic within the range of 20–40. The orientation of support member layer 14 on the shaft 11 is depicted in FIG. 3. As braided, the inner support member layer 14 has a contoured outer surface resulting from weaving of the filaments 30 to form the braid. The density of the braid affects the contour surface shape.

Alternatively, support member layer 14 may comprise at least one filament 30 extending along the length of catheter shaft 11. This filament 30 may extend in a helical fashion about inner tubular member 12 as filament 30 extends along the length of catheter shaft 11. Support member layer 14 may additionally be placed in particular locations over the length of the catheter shaft 11 to add rigidity to these particular portions of the catheter shaft.

While constructing support member layer 14 over inner tubular member 12, filaments 30 may be wrapped around inner tubular member 12 at a tension such that the filaments 30 embed slightly into the inner tubular member 12. A further process for partially embedding the support member layer 14 into the inner tubular member 12 involves heat. In this process, the newly braided catheter is passed through a heated dye that allows filaments 30 to partially embed into inner tubular member 12 without significantly altering the polymeric structure of inner tubular member 12.

Filaments 30 forming the interwoven braid, or extending longitudinally along the length of the catheter, generally have dimensions within the range of 0.0007–0.00125 inches in height and 0.002–0.005 inches in width. Filaments 30 corresponding to these dimensions may be either flat or circular in shape. Furthermore, support member layer 14 may be comprised of either flat or circular filaments 30 exclusively, or a combination may be utilized. Filaments 30 used to form support member layer 14 may also be either high or low tensile.

Suitable filaments 30 for comprising support member layer 14 include, stainless steel wire, polymeric filaments, and alloy metals such as a nickel titanium alloy. It is preferred that at least one filament 30 forming the support member layer 14 comprise tungsten. Tungsten is a radiopaque material. As such, guide catheter 10, or similar medical device comprising at least one tungsten filament 30, is readily discernable within the body under general fluoroscopic observation. However, it has been found that the flexibility characteristics of the support member layer are not acceptable if tungsten is used for all or even a substantial number of the filaments. It has been found necessary to use a combination of stainless steel filaments with the tungsten filaments, with the tungsten filaments comprising no more than half of the total. In preferred embodiments, no more than four tungsten filaments are included in the weave of the braided support member.

Outer tubular member 16 is subsequently formed over support member layer 14. Outer tubular member 16 is generally formed by passing the catheter shaft 11 (having the inner tubular member 12 and support member layer 14) through a second extruder. The second extruder applies a polymer that flows into the interstitial spaces of support member layer 14 and forms a tubular outer layer. Preferably, outer tubular member 16 is comprised of nylon, polyether block amide (PEBA), or a blend of the two. Specifically, the PEBA polymer used to form outer tubular member 16 is PEBAX®, available from ATOMCHEM POLYMERS, Birdsboro, Pa. Prior to extrusion, the material of outer layer may be blended with a liquid crystal polymer (LCP). The mixture may contain about 5% LCP. This has been found to enhance torqueability.

Referring to FIG. 4, a partial cross-sectional side view of the distal portion of outer tubular member 16 after ablation is shown. After the catheter shaft 11 has been processed to include inner tubular member 12, support member layer 14, and outer tubular member 16, the distal portion of the catheter shaft 20 is then modified. Further processing of the distal portion of the catheter shaft 20 permits the guide catheter versatility in particular medical procedures. For instance, a modification that results in a relatively stiff distal portion of the catheter shaft is useful to maximize a guide catheter's response during a coronary procedure.

In order to modify the structural characteristics associated with guide catheter 10, the catheter is first prepped. Prepping guide catheter 10 for modification involves removing the portions of the outer tubular member 16 where the modifications are desired. In reference to FIG. 4, the material being removed is located at the distal portion on the catheter shaft 20. Modifications may be performed at other locations on catheter shaft 11, however, the distal portion is preferred.

Material forming outer tubular member 16 may be removed by various techniques. The technique utilized, however, must allow for the removal of material through the contoured regions of the structural member. In particular, this includes at least a portion of the polymeric material that flowed into the interstitial spaces of braided support member layer 14 during the second extrusion process. In order to achieve this level of specificity during the removal process, the removal process is generally performed by a directed heat source. Heating may be accomplished by any method currently known in the art, including but not limited to, direct current (DC), radiofrequency (RF), inductance, infrared radiation (IR) and electromagnetic radiation (LASER). In a preferred embodiment, material is removed by laser ablation.

The process of laser ablation involves directing a laser at a desired location on catheter shaft 11 and ablating the surrounding outer tubular member material. The laser is guided through outer tubular member 16 and into the region forming structural member layer 14. Material is precisely ablated as to generally follow the contours of the filaments 30 forming the structural member layer 14.

Referring to FIG. 5, a partial perspective view is shown detailing laser ablation of the distal portion of outer tubular member 16. As is shown in the detailed view, the laser first enters into the material forming the outer tubular member 16. The desired depth of ablation by the laser is controlled by the amount of time the laser is in contact with the polymeric material. The laser then proceeds ablating along the length of catheter shaft 11 until a support member layer filament 30 is encountered. Once filament 30 is encountered, the laser does not have sufficient contact time or energy to affect the support member material, so the remaining surface follows the contour of the filament 30, thus effectively reducing the depth of the ablation. The heat generated by the laser may cause the polymeric material of the outer member to flow between strands of the support member, forming a contoured outer surface as generally depicted in FIG. 5. In FIG. 5, portions of the support member filaments are depicted as exposed with no polymeric coating remaining. In practice, however, it is recognized that a thin coating of polymer will remain on the support ember filaments due to cohesion of the polymer to the wire.

The laser ablation procedure generally provides an outer surface following the contours of filament 30. The overall result of the laser ablation process is a series of peaks 37 and valleys 39 ablated within a portion of outer tubular member 16. Peaks 37 are generally identified as the apexes of the filaments (31 and 33) within support member layer 14. All or a portion of the filaments may have a thin polymeric layer overlying them upon completion of the ablation procedure. The areas between filaments (31 and 32), where deeper ablation may occur, comprise the valleys 39. The frequency of the peaks 37 and valleys 39 within the ablated portion of the catheter shaft 11 is directly proportionate to the frequency with which the filament windings occur within the support member layer 14.

Referring to FIG. 6, a partial cross-sectional side view of guide catheter 10 having outer tubular member inserts disposed over the previously ablated region of catheter shaft 70 is shown. Outer tubular member inserts are preferably disposed over the ablated portions of the catheter shaft. Outer tubular member inserts are generally cylindrical in shape. In particular, outer tubular member inserts are defined by the diameter, circumference and altitude they possess.

The outer tubular member inserts additionally comprise an opening in the center of the insert. The diameter of the insert opening is approximately the size of the diameter of support member layer 14. The insert opening allows the inserts to be placed over support member layer 14 and abut the unmodified or unablated portion of the catheter shaft 11. In a preferred embodiment, the insert opening has a diameter approximating the height between a peak 37 and a valley 39 formed through the ablation process. With a diameter of this size, the outer tubular member insert is threaded over the support member layer 14 until the insert abuts the unmodified portion of the catheter shaft 11. Preferably, the outer diameter and circumference of the first outer tubular member insert 51 generally matches those of the unmodified portion of the catheter shaft. Subsequent inserts may additionally conform to these same dimensions. Thus, when adding inserts over the support member layer 14, the transition between the unmodified outer tubular member 16 and the outer tubular member inserts is smooth.

Alternatively, the first outer tubular member insert 51 may comprise a shape described best as a truncated cone. This outer tubular member is defined as having a base, a continuously decreasing diameter and circumference correlated to the altitude of the truncated cone, and possessing a planar surface parallel with the base. Preferably, the truncated planar surface is only marginally smaller than the base of the truncated insert.

Illustrating this embodiment, a truncated insert is desired that possesses a base approximating the dimensions of the unmodified portion of the catheter shaft 11. As such, when abutting the first insert with the unmodified portion of the catheter shaft 11, a generally smooth transition occurs. A second insert, if so desired, will preferably possess a base diameter and circumference that closely approximates the truncated diameter and circumference of the first insert so as to create a second smooth transition. This process may be repeated as necessary to gradually taper the modified portion of the catheter shaft.

Outer tubular member inserts of either form are manufactured with selected physical properties to give a desired durometer as a measure of flexibility. When outer tubular member inserts are assembled upon a modified portion of catheter shaft 11, the physical properties lengths of the individual, or combination of inserts, are transferred to the modified catheter shaft to give a desired flexibility to that region. The physical properties of the inserts, especially flexibility, may be adjusted through varying the materials comprising the inserts. Preferably, the outer tubular inserts are made from various performance grades of PEBA. Some of the inserts may also contain an amount of liquid crystal polymer (LCP) blended therein to increase torqueability. In order to modify the performance (e.g., flexibility) of the inserts, property-enhancing additives may be blended with the PEBA in order to achieve the desired performance characteristics for the individual inserts. Using the various grades of PEBA, an outer tubular member insert may be created having a durometer on the order of 5–90 D. In preferred applications, inserts are on the order of 25–72 D.

In one preferred application, outer tubular inserts may be disposed over the distal portion of the catheter shaft 20, with each subsequent more distal insert having a lower durometer in order to produce a shaft which continues to become more flexible, distally terminating in a soft distal tip 28. The following is an illustration. Referring to FIG. 6, the outer tubular member 16 of the unmodified catheter shaft 11 preferably possesses a durometer of 70 D. The first outer tubular member insert 51, which is placed so that it abuts the unmodified catheter shaft, possesses a durometer of 63 D, which is slightly less than that of the unmodified catheter shaft. The second outer tubular member insert 53, which is even more flexible with a durometer of 55 D, is then positioned over the modified section of the catheter shaft 70 so that it abuts the first outer tubular member insert 51. The third outer tubular member insert 55, having the most flexibility at 30 D, is then subsequently added to the modified catheter shaft 70. In order to complete the distal tip 28, a mandrel 60 is then inserted within the inner tubular member 12 of the distal portion of the catheter shaft 20. Finally, the fourth and last outer tubular member insert 57, also having a durometer of 30 D, is added over mandrel 60 so that it abuts the third outer tubular member insert 55. Because the length of the fourth outer tubular member insert 57 is longer than the remaining modified portion of the catheter shaft 70, the fourth insert 57 is also partially displaced over the mandrel 60 as well.

Once the inserts are properly positioned over the modified section of the catheter shaft 70, the catheter 10 goes though a final manufacturing stage. In this stage of manufacturing, a process sleeve, preferably a heat shrink material, is loaded over the modified 70, and the neighboring unmodified, sections of the catheter shaft 11. These sections are then subjected to a heating source for thermal processing. The temperature from the heating source causes the outer tubular member materials to flow sufficiently to adherer to the shaft and to each other, with the inside surface conforming to the contour surface of the modified shaft. Outer tubular member inserts flow into the peaks 37 and valleys 39 formed during the preparation stage. The fourth outer tubular member insert 57 additionally flows over the mandrel 60 creating a distal tip 28 that covers the exposed distal end of the modified catheter shaft 70. Once cooled, the process sleeve is removed. Furthermore, the mandrel 60 is withdrawn. The result is a modified distal section with a soft distal tip 28.

The peak and valley modification affords the finally processed catheter several advantages. Namely, the modification allows for greater outer tubular member insert retention. Because of the staggered peak and valley shape, inserts are unable to slide longitudinally along the length of the catheter shaft. As a result, the inserts are generally better affixed into position along the catheter shaft.

Furthermore, the peak and valley modification design imparts greater versatility in altering the flexibility of the modified section 70. Because the peaks 37 and valleys 39 are positioned in planes in which the catheter may easily bend, using outer tubular member inserts having a durometer in the range of 5–35 D imparts greater flexibility in the modified region 70.

The same design may also impart significantly less flexibility. Although the peak and valley shape allows for greater bending, the ablated shape also allows for increased polymer volume. To illustrate, in modification procedures involving grinding, material is removed down to the apex of the highest support member layer filament (filaments 31 and 33 in FIG. 5). Outer tubular member material 16 below this apex remains. With laser ablation, however, material lying below the plane of the apex of the highest filament can be removed. As such, the ablation process provides a more voluminous area with which to fill. Thus, filling this area with a less flexible polymer (having a durometer greater than 70 D) thereby imparts a more rigid modified section 70. The modified section 70 would be significantly less flexible than in the catheter's original state, or if the catheter had been modified by grinding.

Referring to FIG. 7, the distal portion of guide catheter 10 illustrating an alternative distal tip 28 is shown. As was described in detail in reference to FIG. 6, outer tubular member inserts are placed over the modified peak and valley section of the catheter shaft 70. The combined length of these inserts, unlike those of FIG. 6, are predetermined so as to approximately end in the same plane as the distal end of the catheter shaft.

In order to complete the distal tip 28, a mandrel 60 is then inserted within the inner tubular member 12 of the distal portion of the catheter shaft 20. Finally, the last outer tubular member insert 59 is added over the mandrel 60 so as to abut both the third outer tubular member insert 53 and the distal end of the catheter shaft. Thus, only last outer tubular member insert 59 is extending over the mandrel 60. Because the last outer tubular member insert 59 is not placed over the modified catheter shaft 70, but rather the mandrel 60 alone, the inner diameter of the last outer tubular member insert 59 is generally smaller than the other inserts.

Using last outer tubular member insert 59 further provides for an alternate tip design having a two-layered distal tip. The first layer 65 is placed over the mandrel 60 and the second layer 66 is placed over the first layer 65. The diameter and circumference of the two-layered insert generally remains the same as the third outer tubular member insert 55 to provide a smooth transition.

The two-layered design provides increased versatility in the distal tip region. In particular, the two-layered design allows for additional transition in flexibility in the distal tip 28. In illustration, in a preferred embodiment, the first layer 65 comprises a durometer having less flexibility (approximately 40 D) than the second layer 66 (approximately 30 D). This configuration retains some stiffness through the centermost region of the catheter 10 for aiding in advancement, while the second layer 66 is more supple to reduce trauma to the surrounding tissue during the catheter's advancement.

Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. A catheter shaft comprising:
   an inner tubular member having a proximal portion, a distal portion, and a lumen extending longitudinally therethrough;
   a support member layer disposed over a substantial portion of the inner tubular member and conforming thereto, the support member layer having a ridged contour comprising peaks and valleys;
   a first outer tubular member disposed over a substantial portion of the support member layer and the inner tubular member and conforming thereto, the first outer tubular member having an outer surface, an inner surface, a proximal portion and a distal portion, the distal portion having an outside diameter less than the outside diameter of the proximal portion, the distal portion disposed over the support member layer so that at least a portion of the outer surface of the first outer tubular member conforms to the ridged contour of the support member layer; and
   a second outer tubular member disposed over at least a portion of the distal portion of the first outer tubular member that follows the contour of the support member layer.

2. The catheter shaft of claim 1, wherein the inner tubular membrane is a lubricious fluorinated polymer.

3. The catheter shaft of claim 2, wherein the fluorinated polymer is perfluoroalkoxy (PFA).

4. The catheter shaft of claim 1, wherein the inner tubular member is extrudable.

5. The catheter shaft of claim 1, wherein the support member layer comprises one or more elongated filaments.

6. The catheter shaft of claim 5, wherein at least one filament comprises tungsten.

7. The catheter shaft of claim 5, wherein the one or more elongated strands are wound to form a braid.

8. The catheter shaft of claim 5, wherein the one or more elongated strands are wound to form a coil.

9. A catheter shaft for a guide catheter, the catheter shaft comprising:
- an inner tubular member having a proximal portion, a distal portion, and a lumen extending longitudinally therethrough;
- a support member layer disposed over a substantial portion of the inner tubular member and conforming thereto, the support member layer having an outside surface including a series of peaks and valleys;
- a first outer tubular member disposed over a substantial portion of the support member layer and the inner tubular member and conforming thereto, the first outer tubular member having an outer surface, an inner surface, a proximal portion and a distal portion, the distal portion having an outside diameter less than the outside diameter of the proximal portion, the distal portion disposed over the support member layer so that at least a portion of the outer surface follows the peaks and valleys formed by the support member layer; and
- a second outer tubular member having an inner surface and an outer surface, the second outer tubular member disposed over at least a portion of the distal portion of the first outer tubular member wherein the inner surface of the second outer tubular member follows the peaks and valleys formed by the support member layer.

10. The catheter shaft of claim 9, wherein the inner tubular membrane is a lubricious fluorinated polymer.

11. The catheter shaft of claim 10, wherein the fluorinated polymer is perfluoroalkoxy (PFA).

12. The catheter shaft of claim 9, wherein the support member layer comprises one or more elongated filaments.

13. The catheter shaft of claim 12, wherein at least one filament comprises tungsten.

\* \* \* \* \*